United States Patent

Berntsson et al.

[11] 4,000,313
[45] Dec. 28, 1976

[54] 1-ISOPROPYLAMINO-3[4'-(2-METHOXY- OR ETHOXY-CARBONYLAMINOETHOXY)-PHENOXY]PROPANOL-2 AND CARDIOSELECTIVE ANTAGONISM USE

[75] Inventors: Peder Bernhard Berntsson, Molndal; Gustav Benny Roger Samuelsson, Molnlycke, both of Sweden

[73] Assignee: Aktiebolaget Hassle, Goteborg, Sweden

[22] Filed: Jan. 22, 1975

[21] Appl. No.: 543,074

[30] Foreign Application Priority Data
Jan. 29, 1974  Sweden ............................ 7402096

[52] U.S. Cl. .................. 424/300; 260/326.14 T; 260/471 C
[51] Int. Cl.² ........................................ C07C 125/06
[58] Field of Search .............................. 260/471 C; 260/326.14 T; 424/300

[56] References Cited
UNITED STATES PATENTS

| | | | |
|---|---|---|---|
| 3,873,600 | 3/1975 | Brandstrom et al. | 260/471 C |
| 3,928,601 | 12/1975 | Brandstrom et al. | 424/300 |
| 3,930,016 | 12/1975 | Berntsson et al. | 424/300 |

*Primary Examiner*—Richard L. Raymond
*Attorney, Agent, or Firm*—Brumbaugh, Graves, Donohue & Raymond

[57] ABSTRACT

Amines of a formula

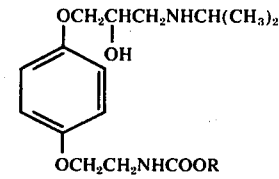

wherein R is methyl or ethyl, as well as processes for their preparation and pharmaceutical compositions containing the same for blocking cardio and vascular β-receptors, and for the treatment of arrhythmia and angina pectoris.

8 Claims, No Drawings

1-ISOPROPYLAMINO-3[4'-(2-METHOXY- OR ETHOXY-CARBONYLAMINOETHOXY)-PHENOXY]PROPANOL-2 AND CARDIOSELECTIVE ANTAGONISM USE

The new compounds have valuable pharmacological properties. Thus, they block cardial β-receptors, which is shown in the determination of the antagonism to tachycardia after an intravenous injection of 0.5 μ/kg of d/1-isoproterenol sulfate to an anaesthetized cat at an intravenous dose of 0.002 to 2 mg/kg. Thus, they block the vascular β-receptors, which is shown in the determination of the antagonism to vasodilation after an intravenous injection of 0.5 μ/kg of d/1 isoproterenol sulfate to an anaesthetized cat at an intravenous dose of 3 mg/kg or more.

The new compounds can be used as cardioselective antagonists to adrenergic β-receptor-stimulators, e.g. in the treatment of arrhythmias and angina pectoris. One may also use them as valuable intermediates in the preparation of other useful compounds, especially pharmaceutically active compounds.

The new compounds can be obtained in accordance with methods known per se.

Thus (method a) a compound of formula II

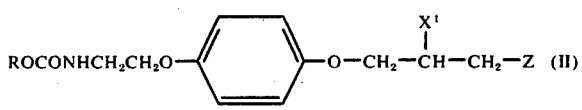

wherein R has the meaning given above, $X^1$ is a hydroxy group, Z is a reactive, esterified hydroxy group, or $X^1$ and Z together form an epoxy group, is reacted with isopropylamine.

A reactive, esterified hydroxy group is particularly a hydroxy group esterified with a strong, inorganic or organic acid, preferably a hydrohalogen acid, such as hydrochloric acid, hydrobromic acid, or hydroiodic acid, further sulfuric acid or a strong organic sulfonic acid such as a strong aromathic sulfonic acid, e.g. benzenesulfonic acid, 4-bromobenzenesulfonic acid or 4-toluenesulfonic acid. Thus, Z is preferably chloro, bromo or iodo.

This reaction is carried out in a known way. When using a reactive ester as a starting material the preparation takes place preferably in the presence of a basic condensing agent and/or with an excess of an amine. Suitable basic condensing agents are e.g. alkali metal hydroxides such as sodium or potassium hydroxide, alkali metal carbonates such as potassium carbonate and alkali metal alcoholates such as sodium methylate, potassium ethylate and potassium tert.-butylate.

Further, (method b) a compound of formula III

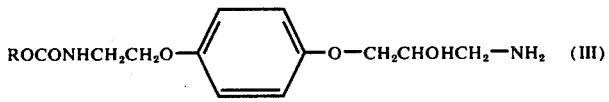

wherein R has the same meaning as given above, is reacted with a compound of formula IV

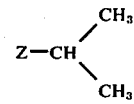

This reaction is carried out in a known way, preferably in the presence of a basic condensing agent and/or an excess of an amine. Suitable basic condensing agents are, e.g. alkaline alcoholates, preferably sodium or potassium alcoholates or also alkaline carbonates such as sodium or potassium carbonate.

Further, (method c) a compound of formula V

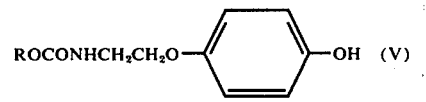

wherein R has the same meaning as given above is reacted with a compound of formula VI

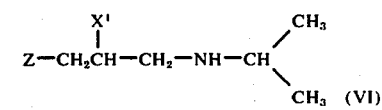

wherein $X^1$ and Z have the same meaning.

This reaction is carried out in a known way. In those cases where reactive esters are used as starting material, the compound of formula V may suitably be used in the form of its metal phenolate, such as alkali metal phenolate, preferably sodium phenolate, or one works in the presence of an acid binding agent, preferably condensing agent, which can form a salt of the compound of formula V, such as an alkali metal alcoholate.

Further, (method d) a compound of formula V may be reacted with a compound of formula VII

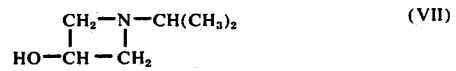

Further, (method e) one may split off a residue from a compound of formula I above, wherein R has the same meaning as above and in which the nitrogen atom(s) of the amino group(s) and/or the hydroxy group have attached thereto a splitable residue.

Such splitable residues are especially those which are splitable by solvolysis, reduction, pyrolysis or fermentation.

Residues splitable by solvolysis are preferably residues splitable by hydrolysis or ammonolysis.

Residues splitable by means of hydrolysis are, e.g., an acyl residue, which, when present, are functionally varied carboxy groups, e.g. oxycarbonyl residues, such as alkoxycarbonyl residues, e.g. tert.-butoxycarbonyl residue, or ethoxycarbonyl residue, aralkoxycarbonyl residues, such as phenyl lower alkoxycarbonyl residues, e.g. a carbobenzyloxy residue halogencarbonyl residue, e.g. a chlorocarbon residue, further arylsulfonyl residues, such as toluenesulfonyl or brom benzenesulfonyl residues and possibly halogenated, such as fluorinate lower alkanoyl residues, such as formyl-, acetylor trifluoroacetyl residue or a benzyl residue, or cyano groups or silyl residues, such as a trimethylsilyl residue.

Of the above mentioned residues present at the hydroxy groups, which residues are splitable by hydrolysis, preferably the oxycarbonyl residues and the lower alkanoyl residues or the benzoyl residues are used.

Besides the above mentioned, also double-bonded residues, which are splitable at the amino group by hydrolysis are used, e.g., alkylidene or benzylidene residue or a phosphorylidene group such as a triphenyl-phosphorylidene group, whereby the nitrogen atom then obtains a positive charge.

Residues splitable at the hydroxy group and the amino group by hydrolysis are furthermore divalent residues as in occurring cases substituted methylene. As substituents on the methylene residues any organic residue may be used, wherein it does not matter in the hydrolysis which compound is the substituent on the methylene residue. As methylene substituents, e.g., aliphatic or aromatic residues such as alkyl as mentioned above, aryl, e.g., phenyl or pyridyl, may be used. The hydrolysis may be carried out in any known way suitably in a basic or preferably in an acid medium.

Compounds having residues which are splitable by hydrolysis are also the compounds according to formula VIII

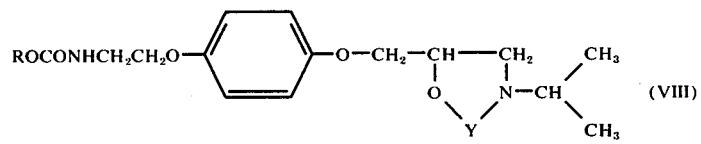

wherein R has the same meaning as given above and Y is a carbonyl or thiocarbonyl residue.

The hydrolysis is carried out in an analogous way, e.g. in the presence of a hydrolyzing agent, e.g., in the presence of an acidic agent such as diluted mineral acids such as sulfuric acid or hydrohalogen acid, or in the presence of basic agents such as e.g., alkali metal hydroxides, such as sodium hydroxide. Oxycarbonyl residues, aryl sulfonyl residues and cyano groups may in a suitable way be split off by means of acidic agents as by means of a hydrohalogen acid, suitably hydrobromic acid. Preferably, the splitting may take place using diluted hydrobromic acid, possibly in a mixture with acetic acid. Cyano groups are preferably split off by means of hydrobromic acid at an elevated temperature, as in boiling hydrobromic acid, according to the "bromocyano method" (v. Braun). Further, e.g., a tert.-butoxycarbonyl residue may be split off under anhydrous conditions by means of a treatment with a suitable acid, such as trifluoracetic acid. Acidic agents are preferably used in the hydrolysis of compounds of formula VIII.

Residues splitable by ammonolysis are especially the halogen carbonyl residues, such as the chlorocarbonyl residue. The ammonolysis may be carried out in a known way, e.g., by means of an amine containing at least one hydrogen atom bonded to the nitrogen atom, such as a mono- or diloweralkylamine, e.g., methylamine or dimethylamine, or especially ammonia, preferably at an elevated temperature. Instead of ammonia one may use an agent which gives ammonia, such as hexamethylene tetra amine.

Residues splitable by means of reduction are, e.g., an α-arylalkyl residue, such as a benzyl residue or an α-aralkoxycarbonyl residue such as a benzyloxycarbonyl residue, which in a known way may be split off by means of hydrogenolysis, especially by catalytically activated hydrogen, as by hydrogen in the presence of hydrogenating catalysts, e.g., Raney-nickel. Further residues splitable by means of hydrogenolysis are 2-halogenalkoxycarbonyl residues such as 2,2,2-trichloroethoxycarbonyl residues or 2-iodoethoxy- or 2,2,2-tri-bromoethoxycarbonyl residues, which may be split off in a known way, suitably by means of metallic reduction (so-called nascent hydrogen). Nascent hydrogen may be obtained by the influence of metal or metal alloys, such as amalgam on compounds which give hydrogen, such as carboxy acids, alcohols or water, whereby especially zinc or zinc alloys together with acetic acid may be used. Hydrogenolysis of 2-halogenalkoxy carbonyl residues may further take place using chromium or chromium (II) compounds such as chromium (II) chloride or chromium (II) acetate.

A residue splitable by reduction may also be an arylsulfonyl group, such as a toluenesulfonyl group, which in a known way may be split off by reduction using nascent hydrogen, e.g., by means of an alkali metal, such as lithium or sodium in liquid ammonia, and suitably may be split off from a nitrogen atom. In carrying out the reduction one has to take care of the face that other reducible groups are not affected.

Residues splitable by means of pyrolysis, especially residues splitable from the nitrogen atom, are in occurring cases substituted, suitably unsubstituted carbamoyl groups. Suitable substituents are, e.g., loweralkyl or arylloweralkyl such as methyl or benzyl, or aryl, such as phenyl, the pyrolysis is carried out in a known way, wherein one may have to take care of other thermally suspectible groups.

Residues splitable by means of fermentation, especially residues splitable from the nitrogen atom, are in occurring cases substituted, however, suitably unsubstituted carbamoyl groups. Suitable substituents are, e.g., loweralkyl or arylloweralkyl, such as methyl or benzyl, or aryl, such as phenyl. The fermentation is carried out in a known way, e.g., by means of the enzyme urease or soy bean extract at about 20° C or a slightly elevated temperature.

Further, (method f) a Schiff's base of formula IX or X

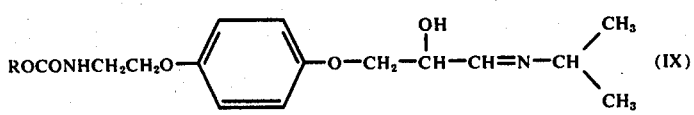 (IX)

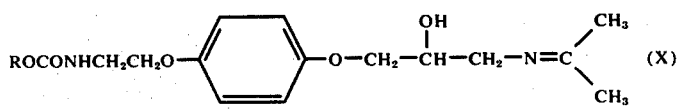 (X)

or a cyclic tautomer corresponding to formula X of formula XI

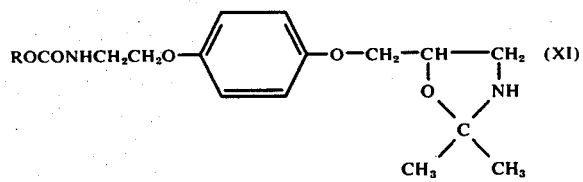 (XI)

can be reduced, wherein R has the same meaning as given above, and whereby the compounds of formula X and XI may exist together, too. This reduction is carried out in a known way, e.g., using a dilightmetal hydride, such as sodiumborohydride, lithium aluminium hydride, with a hydride such as boran, with a formic acid, or by means of catalytic hydrogenation, as with hydrogen in the presence of Raney-nickel. In the reduction one has to take care that other groups are not affected.

Further, (method g) in a compound of formula XII

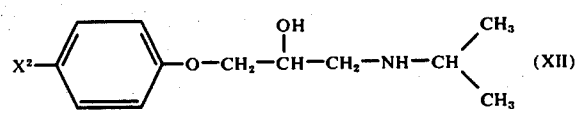 (XII)

wherein $X^2$ is a residue transformable into a residue ROCONHCH$_2$CH$_2$O with the meaning given above, one transforms $X^2$ into ROCONHCH$_2$CH$_2$O. A residue $X^2$ transformable into ROCONHCH$_2$ CH$_2$O is, e.g., a residue Z—CH$_2$ CH$_2$O, whereby Z has the meaning given above. A compound XII having such a residue Z—CH$_2$CH$_2$O as $X^2$ can be reacted with a compound ROCONH$_2$ in a way known per se. Thus, one can react a compound of formula XIII

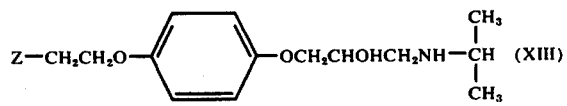 (XIII)

with a compound ROCONH$_2$, wherein R and Z have the same meanings as given above. The reaction is carried out in a known way, e.g., as the reaction according to method (a) of formula II with isopropylamine.

A residue $X^2$ transformable into ROCONHCH$_2$CH$_2$O is, e.g., the residue H$_2$NCH$_2$CH$_2$O. A compound XII having such a residue H$_2$NCH$_2$CH$_2$O as $X^2$ can be reacted in a known way with a compound ROCOCl. Thus, a compound of formula XIV

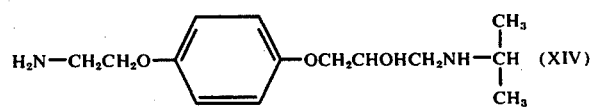 (XIV)

can be reacted with a compound ROCOCl, wherein R has the same meaning as given above. The reaction is carried out in a known way, e.g., as the reaction according to method (a) of a compound of formula II with isopropylamine.

A residue $X^2$ transformable into ROCONHCH$_2$CH$_2$O is e.g., a residue $Z^1$—CONHCH$_2$CH$_2$O. A compound XII having such a residue $Z^1$—CONHCH$_2$CH$_2$O can in a known way be reacted with a compound R—$Z^2$, wherein one of $Z^1$ and $Z^2$ is a hydroxy and the other is Z having the meaning given above.

Thus, one can react a compound of formula XV

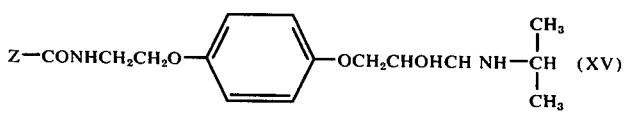

with a compound R—OH, wherein R and Z have the same meanings as given above. The reaction is carried out in a known way, e.g., as the reaction according to method (a) of a compound of formula II with isopropylamine.

A compound of formula XII having a hydroxy group as the residue $X^2$ can be reacted in a known way with a compound $ROCONHCH_2CH_2$—Z, wherein Z has the meaning given above. Thus, one can react a compound of formula XVI

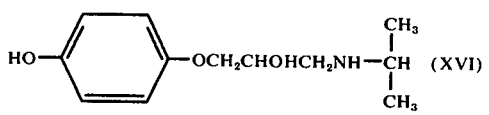

with a compound $ROCONHCH_2CH_2$—Z, wherein R and Z have the same meanings as given above. The reaction is carried out in a known way, e.g., as the reaction according to method (a) of a compound of formula II with isopropylamine.

One can also (method h), in a suitable way, hydrogenate an amine of formula XVII

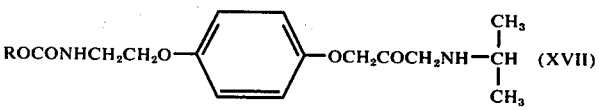

In a known way the substituents may be varied from the compounds obtained within the end product, or the compounds obtained may be introduced, split off or transformed into other end products in a known way.

Thus, it is possible to hydrogenate catalytically C = C double bonds or triple bonds to C ≡ C triple bonds to C - C single bonds by means of hydrogen in the presence of a hydrogenation catalyst, e.g., platinum, palladium or nickel, such as Raney-nickel. In such methods, one has to be sure that other reducable groups are not reduced.

In compounds obtained containing a C ≡ C triple bond this may further be transformed into a C = C double bond and, if desired, be hydrogenated stereo-specifically into a C = C - cis or C = C - trans double bond. The hydrogenation of a C ≡ C triple bond to a C = C double bond may, for example, be carried out using 1 mole of hydrogen in the presence of a less active hydrogenation catalyst, such as iron or palladium, e.g., Raney-iron or palladium with barium sulfate, preferably at an elevated temperature. The hydrogenation to a C = C - cis double bond may take place, e.g., between 1 mole of hydrogen and a deactivated catalyst, such as palladium on active carbon and in the presence of quinoline, palladium on calcium carbonate in the presence of lead salts or Raney-nickel. The hydrogenation to a C = C - trans double bond may take place by means of sodium of liquid ammonia, wherein with regard to other reducable groups, short reaction times are used and no excess of the reducing agent is uses, possibly an ammonium halogenide, such as ammonium chloride, being added as a catalyst.

In the reduction mentioned above one has to take care that no other reducable groups are reduced.

The above mentioned reactions may possibly be carried out simultaneously or seriatum in any sequence.

The above mentioned reactions are carried out in a manner known per se in the presence or absence of diluting, condensing and/or catalytic agents at a low, room or an elevated temperature, possibly being carried out in a closed vessel.

Depending on the process conditions and the starting material, the end product is obtained either in free form or in the form of its acid addition salt, which is included in the scope of the invention. Thus, for example, basic, neutral or mixed salts may be obtained as well as hemiamine, sesquior polyhydrates. The acid addition salts of the new compounds may in a manner known per se be transformed into free compounds using, e.g., basic agents such as an alkali or an ion exchanger. On the other hand, the free bases obtained may form salts with organic or inorganic acids. In the preparation of acid addition salts, preferably those acids are used which form suitable therapeutically acceptable salts. Such acids are, e.g., hydrohalogen acids, sulfuric acids, phosphoric acid, nitric acid, perchloric acid, aliphatic, alicyclic, aromatic or heterocyclic, carboxy or sulfonic acids, such as formic, or acetic, propionic, succinic, glycolic, lactic, malic, tartaric, citric, ascorbic, maleic, hydroxymaleic or pyruvic acid, phenylacetic, benzoic, p-aminobenzoic, anthranilic, p-hydroxybenzoic, salicylic or p-aminosalicyclic acid, embonic acid, methanesulfonic, ethanesulfonic, hydroxyethanesulfonic, ethylenesulfonic acids, halogenbenzenesulfonic toluenesulfonic, naphthylsulfonic acids, or sulfanilic acid; methionine, tryptophane, lysine or arginine.

These or other salts of the new compounds such as, e.g., picrates may serve as purifying agents of the free bases obtained. The free bases are transformed into salts, these are separated, and the bases are then set free from the salts again. Due to the close relationship between the new compounds in free form and in the form of their salts it will be understood from the foregoing and the following that, if possible, the corresponding salts are included in the discussion of the free compounds.

The invention also relates to any embodiment of the process in which one starts from any compound obtained as an intermediate in any process step and one carries out the remaining process step, or one breaks off the process at any step, or in which one forms a starting material under the reaction conditions, or in which a reaction component, possibly in the form of its salt, is present.

Thus, one may react an aldehyde of the formula XVIII

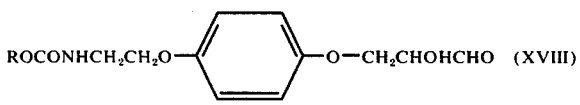

wherein R has the same meaning as given above, with isopropylamine in the presence of a suitable reducing agent, as one of the above mentioned. Thereby, a compound of formula IX is obtained as an intermediate, which then is reduced according to the invention.

Further, one may in a manner known per se react an amine of the formula III with acetone, in the presence of a suitable reducing agent, such as one of the above mentioned. Thereby, a compound of formula X or XI is obtained as an intermediate, which then is reduced according to the invention.

The new compounds may, depending on the choice of starting materials and process, be present as optical antipodes or racemate, or, if they contain at least two asymmetric carbon atoms, be present as an isomeric mixture (racemate mixture).

The isomeric mixtures (racemic mixtures) obtained may, depending upon physical-chemical differences of the components, be separated into both stereoisomers (diastereomeric) pure racemate, e.g., by means of chromotography and/or fractional crystallization.

The racemates obtained can be separated according to known methods, e.g., by means of recrystallization from an optically active solvent, by means of microorganisms, or by reaction with optically active acids forming salts of the compound and separating the salts thus obtained, e.g., by means of their different solubility in the diastereomers, from which the antipodes may be set free by the influence of a suitably agent. Suitably usable optically active acids are, e.g., the L- and D- forms of tartaric acid, di-o-tolyltartaric acid, malic acid, mandelic acid, camphorsulfonic acid or china acid. Preferably, the more active part of the two antipodes is isolated.

Suitably, such starting materials are used for carrying out the reactions of the invention, which material leads to groups of end products primarily especially desired, and especially to the specifically described and preferred end products.

The starting materials are known or may, if they should be new, be obtained according to processes known per se.

In clinical use the compounds of the invention are administered normally orally, rectally or by injection in the form of a pharmaceutical preparation, which contains an active component either as the free base or as a pharmaceutically acceptable, non-toxic addition salt, as e.g., the hydrochloride, lactate, acetate, sulfamate or the like, in combination with a pharmaceutically acceptable carrier. When the new compounds of the invention are mentioned herein we intend either the free amine or the acid addition salts of the free base, even if the compounds are generally or specifically described, provided that the context permits. The carrier may be a solid, semisolid or liquid diluent or a capsule. These pharmaceutical preparations are a further object of the invention. Usually the amount of active compound is between 0.1 to 95% by weight of the preparation, suitably between 0.5 to 20% by weight in preparations for injection and between 2 to 50% by weight in preparations for oral administration.

In the preparation of pharmaceutical preparations containing a compound of the present invention in the form of dosage units for oral administration the compound chosen may be mixed with a solid, pulverulent carrier, as e.g., with lactose, saccharose, sorbitol, mannitol, starch, such as potato starch, corn starch amylopectin, cellulose derivatives or gelatine, as well as with an antifricton agent, such as magnesium stearate, calcium stearate, polyethyleneglycol waxes or the like, and be pressed into tablets. If coated tablets are desired, the core, prepared as above, may be coated with a concentrated solution of sugar, which solution may contain, e.g., gum arabicum, gelatine, talc, titaniumdioxide or the like. Furthermore, the tablets may be coated with a lacquer dissolved in an easily volatile organic solvent or mixture of solvents. To this coating, a dye may be added in order to easily distinguish between tablets with different active compounds or with different amounts of the active compound present.

In the preparation of soft gelatine capsules (pearl-shaped, closed capsules), which consist of gelatine and, e.g., glycerine, or in the preparation of similar closed capsules the active compound is mixed with a vegetable oil. Hard gelatine capsules may contain granules of the active compound in combination with a solid, pulverulent carrier such as lactose, saccharose, sorbitol, mannitol, starch (as e.g., potato starch, corn starch or amylopectin), cellulose derivatives or gelatine.

Dosage units for rectal administration may be prepared in the form of suppositories, which contain the active substance in a mixture with a neutral fat base, or they may be prepared in the form of gelatine-rectal capsules which contain the active substance in a mixture with a vegetable oil or paraffin oil.

Liquid preparations for oral administration may be in the form of syrups or suspensions, e.g., solutions containing from about 0.2% by weight to about 20% by weight of the active substance described, wherein the residue consists of sugar and a mixture of ethanol, glycerol and propylene glycol. If desired, such liquid preparations may contain coloring agents, flavoring agents, saccharin and carboxymethylcellulose as a thickening agent.

Solutions for parenteral administration by injection may be prepared as an aqueous solution of a water soluble pharmaceutically acceptable salt of the active compound, preferably in a concentration from about 0.5% by weight to about 0.10% be weight. These solutions may also contain stabilizing agents and/or buffering agents and may suitably be available in different dosage unit ampoules.

The preparation of pharmaceutical tablets for peroral use is carried out in accordance with the following method:

The solid substances included are ground or sieved to a certain particle size. The binding agent is homogenized and suspended in a certain amount of solvent. The therapeutic compound and necessary auxiliary agents are mixed with continuous and constant mixing with the binding agent solution and are moistened so that the solution is uniformly divided in the mass without overmoistening any part. The amount of solvent is usually such that the mass obtains a consistency similar to wet snow. The moistening of the pulverulent mixture with the binding agent solution causes the particles to gather together slightly into aggregates and the real granulating process is carried out in such a way that the mass is pressed through a sieve in the form of a net of stainless steel having a mesh size of about 1 mm. The mass is then placed in thin layers on a tray to be dried in a drying cabinet. This drying takes place during 10 hours and has to be standardized carefully as the liquid content of the granulate is of utmost importance for the following process and for the features of the tablets. Drying in a fluid bed may possibly be used. In this case, the mass is not put on a tray but is poured into a container having a net bottom.

After the drying step the granules are seived so that the desired particle size is obtained. Under certain circumstances powder has to be removed.

To the so-called final mixture, disintegrating, antifriction agents and antiadhesive agents are added. After this mixture is made the mass should have its correct composition for the tableting step.

The cleaned tablet punching machine is provided with a certain set of punches and dies, whereupon a suitable adjustment for the weight of the tablets and the degree of compression is tested out. The weight of the tablet is decisive for the size of the dose in each tablet and is calculated starting from the amount of therapeutic agent in the granules. The degree of compression affects the size of the tablet, its strength and its ability of disintegration in water. Especially as regards the two latter properties, the choice of compression pressure (0.5 to 5 ton) requires a balancing of factors. When the correct adjustment is set, the preparation of tablets is started and is carried out at a rate of 20,000 to 200,000 tablets per hour. The pressing of the tablets requires different times and depends on the size of the batch.

The tablets are freed from adhering powder in a specific apparatus and are then stored in closed packages until they are shipped.

Many tablets, especially those which are rough or bitter, are coated with a coating. This means that such tablets are coated with a layer of sugar or some other suitable coating.

The tablets are usually packed by machines which have an electronic counting device. The different types of packages include glass or plastic gallipots, or boxes, tubes and specific dosage-adapted packages.

The daily dose of the active substance varies and depends on the type of administration, but as a general rule it is 100 to 400 mg/day of active substance for peroral administration, and 5 to 20 mg/day for intravenous administration.

The following illustrates the principle and the adaptations of invention, however, the invention is not limited thereto. Temperature is given in degrees Centigrade.

EXAMPLE 1

4.1 g of 1.2-epoxy-3-[4-(methoxycarbonylaminoethoxy)phenoxy]propane were mixed with 4.1 ml. isopropylamine and 2.5 ml of isopropanol. The mixture was refluxed for 3 hours and evaporated to dryness. The residue was dissolved in 2 M hydrochloric acid and the mixture was washed twice with ether. The aqueous phase was made alkaline with sodium hydroxide and extracted with methylene chloride. After drying and evaporation and residue was dissolved in ethyl acetate, and ether containing HCl was added to pH 4. The hydrochloride was filtered off and isolated after having been recrystallized from acetone. 2.6 g of 1-isopropylamino-3-[4 -(2-methoxycarbonylaminoethoxy)-phenoxy]-propanol-2 hydrochloride were obtained. Melting point 108° C. The structure was determined using NMR.

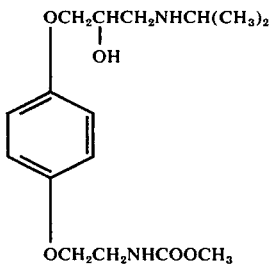

EXAMPLE 2

The material given in Example 1 was prepared in accordance with the following. 20.0 g. of N,N-dibenzyl-2-chloroethylamine hydrochloride and 27.6 g of potassium carbonate were mixed in 250 ml of acetonitrile. The mixture was refluxed for 15 min. and 13.8 g of 4-benzyloxyphenol were added, whereupon the mixture was refluxed for 5 hours while stirred. After filtration and evaporation the residue was recrystallized from petroleum ether. 18.4 g of 1-(N,N-dibenzylamino)-2-(4-benzyloxyphenoxy)-ethane was obtained. The structure was determined using NMR.

The product obtained was dissolved in 185 ml of 95% ethanol and 5.5 ml of conc. HCl. After hydrogenation over Pd/C-catalyst, filtration, evaporation, and recrystallization from isopropanol/ether, 5.8 g of 4-aminoethoxyphenol was obtained. Melting point 175° C. The structure was determined using NMR.

The 4-aminoethoxyphenol obtained and 6.3 g of sodium bicarbonate were mixed in 25 ml of water and cooled on an icebath. 5.3 g of chloroformic acid methylester were added while stirring. The mixture was stirred at room temperature for 3 hours and then extracted with methylene chloride. The methylene chloride phase was dried and evaporated. The diacylated product thus obtained was then hydrolyzed overnight with a 2 M sodium hydroxide solution. The mixture was acidified with hydrochloric acid and extracted with methylene chloride. After drying and evaporation 3.9 g 4-methoxycarbonylaminoethoxyphenol was obtained as a yellow oil. The structure was determined using NMR.

The p-methoxycarbonylaminoethoxyphenol thus obtained was dissolved in 30 ml of epichlorohydrin and 1.8 g of potassium carbonate were added. The mixture was refluxed for 2 hours. After filtration and evaporation 4.1 g of 1,2-epoxy-3-(4 -methoxycarbonylaminoethoxyphenoxy)-propane were obtained as an oil which crystallized. Melting point 65° C. The structure was determined using NMR.

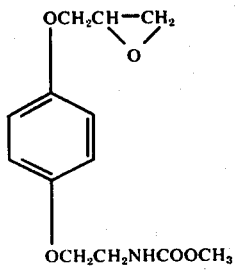

EXAMPLE 3

(Method B)

10 g of 4-(2-methoxycarbonylaminoethoxy)-phenylglycidylether in 100 ml of ethanol were saturated with gaseous ammonia and the mixture was heated in an autoclave on a boiling water bath for 4 hours. The solvent was evaporated and the residue was dissolved in ethylacetate and HCl-gas was introduced. The hydrochloride then precipitated and it was filtered off and dissolved in 50 ml of ethanol to which isopropylamine and 15 g of $K_2CO_3$ had been added. The mixture was heated in an autoclave at 130° C for 10 hours whereupon the solvent was evaporated and the residue was mixed with 100 ml of 2N HCl and 100 ml of ether. The aqueous phase was separated off and was made alkaline with 2N NaOH and extracted with ethyl acetate. The solvent phase was dried over $K_2CO_3$, whereupon 1-isopropylamine-3-[4-(2-methoxycarbonylaminoethoxy)-phenoxy]propanol-2 was converted to its hydrochloride by introducing ether containing HCl to pH 4 and recrystallized from acetone. Melting point 108° C.

EXAMPLE 4

(Method C)

2.4 g of Na were dissolved in 100 ml of ethanol, whereupon 19.0 g of 4-(2-methoxycarbonylaminoethoxy)phenol and 15.5 g of 1-isopropylamino-3-chloropropanol-2 were added. The mixture was heated in an autoclave on a boiling water bath for 15 hours. Thereupon it was filtered and the filtrate was evaporated to dryness. The residue was made acidic with 2N HCl and extracted with ether, whereupon the aqueous phase was made alkaline with 2N NaOH and extracted with ethylacetate. The ethylacetate was dried over $MgSO_4$ and 1-(isopropylamino-3-[4-(2-methoxycarbonylaminoethoxy)-phenoxy]-propanol-2 was converted to its hydrochloride in accordance with Example 1 above. Melting point 107° C.

EXAMPLE 5

(Method E)

In accordance with Example 4 above, N-benzyl-1-isopropylamino-3-[4-(2-methoxycarbonylaminoethoxy)-phenoxy]propanol-2 was prepared from 4-(2-methoxycarbonylaminoethoxy) phenol and N-benzyl-1-isopropylamino-3-chloropropanol-2 p-hydroxybenzoate, 10 g of the compound thus obtained were dissolved in 100 ml of ethanol, 0.5 g of Pd/C (10%) catalyst were added and hydrogenation was carried out until the estimated amount of $H_2$ had been absorbed. After filtration the mixture was evaporated to dryness and the residue 1-isopropylamino-3-[4-(2-methoxycarbonylaminoethoxy)phenoxy]propanol-2 was converted to its hydrochloride in accordance with Example 1 above. Melting Point 108° C.

EXAMPLE 6

(Method F)

11 g of 1-amino-3-[4-(2-methoxycarbonylaminoethoxy) phenoxy]-propanol-2 prepared in accordance with Example 3 above were dissolved in 80 ml of methanol containing 5 g of acetone. The solution was cooled on an ice bath and 10 g of sodium borohydride was added little by little. The temperature was allowed to rise to room temperature and after 1 hour 200 ml of $H_2O$ were added and the mixture was extracted with ethylacetate The ethylacetate phase was dried over $K_2CO_3$ and the compound 1-isopropylamino-3-[4-(2-methoxycarbonylaminoethoxy)-phenoxy]propanol-2 was converted to its hydrochloride by introducing ether containing HCl to pH 4, isolating the precipitate and recrystallizing it from acetone. Melting point 108° C.

EXAMPLE 7

(Method G)

10 g of 1-isopropylamino-3-[4-(2-chloroethoxyphenoxy]propanol-2, 8 g of methoxycarbonylamine and 15 g of $K_2CO_3$ were mixed in 100 ml of acetonitrile and were refluxed for 5 hours while stirring. Filtration and evaporation gave crude 1-isopropylamino-3-[4-(2-methoxycarbonylaminoethoxy)phenoxy]-propanol-2 which was dissolved in ethylacetate and transformed to its hydrochloride by introducing ether containing HCl and recrystallizing the precipitate from acetone. Melting point 108° C.

EXAMPLE 8

(Method D)

0.116 moles of 4-methoxycarbonylaminoethoxyphenol were mixed with 0.080 moles of 1-isopropyl-3-acetidinol, 0.500 moles of benzyl alcohol and 0.003 moles of KOH. The mixture was refluxed at 140° C for 6 hours while being stirred and then cooled and extracted with 2 M HCl. The aqueous phase was made alkaline and then extracted with chloroform. After drying and evaporation the residue was dissolved in ether and to the solution ether containing HCl was added. The hydrochloride was filtered off and washed with acetone. The hydrochloride of 1-isopropylamino-3-[4 -(2-methoxycarbonylaminoethoxy)-phenoxy]-propanol-2 was obtained. Melting point 108° C.

EXAMPLE 9

A syrup containing 2% (weight per volume) of active substance was prepared from the following ingredients:

| | |
|---|---|
| 1-isopropylamino-3-[4-(2-methoxy-carbonylaminoethoxy)phenoxy]-propanol-2 . HCl | 2.0 g |
| Saccharine | 0.6 g |
| Sugar | 30.0 g |
| Glycerine | 5.0 g |
| Flavoring agent | 0.1 g |
| Ethanol 96% | 10.0 ml |
| Distilled water | ad 100.0 ml |

Sugar, saccharine and the ether salt were dissolved in 60 g of warm water. After cooling, glycerine and a solution of flavoring agents dissolved in ethanol were added. To the mixture water was then added to 100 ml.

The above given active substance may be replaced with other pharmaceutically acceptable acid addition salts.

EXAMPLE 10

1-isopropylamino-3-[4-(2-methoxycarbonylaminoethoxy)-phenoxy]-propanol-2 hydrochloride (250 g) was mixed with lactose (175.8 g), potato starch (169.7 g) and colloidal silicic acid (32 g). The mixture was moistened with a 10% solution of gelatine and was granulated through a 12-mesh sieve. After drying, potato starch (160 g), talc (50 g) and magnesium stearate (5 g) were admixed and the mixture thus obtained was pressed into tablets (10,000) which contain 25 mg of substance. The tablets are sold on the market provided with a breaking score to give another does than 25 mg or to give multiples thereof when broken.

EXAMPLE 11

Granules were prepared from 1-isopropylamino-3-[4-(2-methoxycarbonylaminoethoxy)-phenoxy]-propanol-2-hydrochloride (250 g), lactose (175.9 g) and an alcoholic solution of polyvinylpyrrolidone (25 g). After the drying step, the granules were mixed with talc (25 g), potato starch (40 g), and magnesium stearate (2.50 g) and was pressed into 10,000 biconvex tablets. These tablets are primaryily coated with a 10% alcoholic solution of shellac and thereupon with an aqueous solution containing saccharose (45%), gum arabicum (5%), gelatine (4%) and dyestuff (0.2%). Talc and powdered sugar were used for powdering after the first five coatings. The coating was then coated with a 66% sugar syrup and polished with a 10% carnauba wax solution in carbon tetrachloride.

EXAMPLE 12

1-isopropylamino-3-[4-(2-methoxycarbonylaminoethoxy)phenoxy]-propanol-2-hydrochloride (1 g), sodium chloride (0.8 g) and ascorbic acid (0.1 g) were dissolved in sufficient amount of distilled water to give 100 ml. of solution. This solution, which contains 10 mg of active substance on each ml, was used in filling ampoules, which were sterilized by heating at 120° C for 20 minutes.

We claim:
1. An amine of the formula

wherein R is methyl or ethyl or a pharmacologically acceptable addition salt of said amine.

2. 1-isopropylamino-3-[4'-(2-methoxycarbonylaminoethoxy)-phenoxy]-propanol-2.

3. A compound according to claim 1 in the form of its dextro-rotating optical antipode.

4. A compound according to claim 1 in the form of its levo-rotating optical antipode.

5. A compound according to claim 1 in the form of its free base.

6. A compound according to claim 1 in the form of a pharmacologically acceptable addition salt.

7. A pharmaceutical composition providing cardioselective antagonism to adrenergic β-receptor stimulation containing as an active ingredient a compound according to claim 1, together with a therapeutically acceptable carrier.

8. A method for providing cardioselective antagonism to adrenergic β-receptor stimulation in an animal subject which comprises administering to said subject, in an amount effective to provide said cardioselective antagonism to adrenergic β-receptor stimulation, at least one compound according to claim 1.

* * * * *